(12) United States Patent
Lin et al.

(10) Patent No.: US 10,865,377 B2
(45) Date of Patent: Dec. 15, 2020

(54) CORDYCEPS CICADAE MYCELIUM ACTIVE SUBSTANCES, PREPARATION METHOD, PHARMACEUTICAL COMPOSITION AND APPLICATION THEREOF

(71) Applicant: GRAPE KING BIO LTD., Zhong-Li (TW)

(72) Inventors: Pei-Cheng Lin, Zhong-Li (TW); Han-Hsin Chang, Zhong-Li (TW); Chin-Chu Chen, Zhong-Li (TW); Shu-Hsing Yeh, Zhong-Li (TW); Li-Ya Lee, Zhong-Li (TW); Jui-Hsia Hsu, Zhong-Li (TW)

(73) Assignee: GRAPE KING BIO LTD., Zhong-Li (TW)

( * ) Notice: Subject to any disclaimer, the term of this patent is extended or adjusted under 35 U.S.C. 154(b) by 208 days.

(21) Appl. No.: 15/896,752

(22) Filed: Feb. 14, 2018

(65) Prior Publication Data
US 2018/0171282 A1 Jun. 21, 2018

Related U.S. Application Data

(62) Division of application No. 14/939,698, filed on Nov. 12, 2015, now abandoned.

(30) Foreign Application Priority Data

Apr. 22, 2015 (TW) .............................. 104112814 A

(51) Int. Cl.
| | | |
|---|---|---|
| *C12N 1/14* | (2006.01) | |
| *C12P 1/02* | (2006.01) | |
| *A61K 36/06* | (2006.01) | |
| *A61K 35/66* | (2015.01) | |
| *A61K 36/068* | (2006.01) | |

(52) U.S. Cl.
CPC ................ *C12N 1/14* (2013.01); *A61K 35/66* (2013.01); *A61K 36/068* (2013.01); *C12P 1/02* (2013.01)

(58) Field of Classification Search
CPC ........ A61K 36/06; A61K 36/068; C12N 1/14; C12P 1/02
See application file for complete search history.

(56) References Cited

PUBLICATIONS

Zhu et al., "Cordyceps cicadae extracts ameliorate renal malfunction in a remnant kidney model," Journal of Zhejiang University—Science B (Biomed & Biotechnol), 2011, vol. 12, No. 12, pp. 1024-1033.

*Primary Examiner* — Robert J Yamasaki
*Assistant Examiner* — Charles Zoltan Constantine
(74) *Attorney, Agent, or Firm* — .Birch, Stewart, Kolasch & Birch, LLP

(57) ABSTRACT

A method of preparing *Cordyceps cicadae* mycelium active substances for preventing and/or treating xerophthalmia is provided. The method comprises: (a) culturing a *Cordyceps cicadae* mycelium in a plate media at 15 to 35° C. for 5 to 14 days; (b) inoculating the mycelium of step (a) to a flask containing liquid media and culturing it at 15 to 35° C. with a pH of 2 to 8 for 3 days; (c) inoculating the mycelium of step (b) to a fermenter tank and culturing it at 15 to 35° C. with a pH of 2 to 8 for 3 days, so as to obtain a *Cordyceps cicadae* mycelium fermentation liquid; (d) freeze-drying and grating the fermentation liquid, so as to obtain a *Cordyceps cicadae* mycelium powder; (e) extracting the powder with solvent, so as to obtain a *Cordyceps cicadae* mycelium extract; and (f) drying the extract, so as to obtained the *Cordyceps cicadae* mycelium active substances.

9 Claims, 10 Drawing Sheets

*CORDYCEPS CICADAE* MYCELIUM ACTIVE SUBSTANCES, PREPARATION METHOD, PHARMACEUTICAL COMPOSITION AND APPLICATION THEREOF

CROSS-REFERENCE TO RELATED APPLICATION

This application is a divisional application of U.S. patent application Ser. No. 14/939,698, filed Nov. 12, 2015, which claims priority under 35 U.S.C. § 119(a) to Patent Application No. 104112814 filed in Taiwan on Apr. 22, 2015, all of which are hereby expressly incorporated by reference into the present application.

BACKGROUND

Technical Field

The present invention relates the development of *Cordyceps cicadae* (*C. cicadae*) mycelium active substances, in particularly relates to the application for preventing and/or treating xerophthalmia induced by physical or chemical injuries.

Description of Related Art

Dry Eye Syndrome (Xerophthalmia)

"Xerophthalmia" is a common disease in Ophthalmology (eye) clinic (10-15% adult). Xerophthalmia is mainly caused by a deficiency of tears or abnormal tear composition. The general symptoms of xerophthalmia include eye dryness, fatigue, sleepiness, foreign body sensation, itching, burning and pain sensations, heavy eyelids, sticky secretions, photophobia, increased wind and external stimuli sensitivities, transient blurred vision, and excessive tearing. The severe symptoms of xerophthalmia include red, swollen, congestion, horny eye, corneal ulcer and conjunctivitis, which might affect vision if left untreated. The causes of deficiency of tears are many: tired eyes, wear contact lens for a long time, ocular inflammation, normal aging process, hormonal imbalances, autoimmune diseases, diabetes, etc. As xerophthalmia is a multi-faceted problem, it is also called as dry eye syndrome.

Composition and Function of Tears

There is a tear film on the normal ocular surface. Tear film covers the cornea and conjunctiva so as to protect and lubricate the eyes. The old tear film and excess tears flow through nasolacrimal duct. Tear film comprises three layers:

Oil (Lipid) Layer:

This lipid layer produced by the meibomian glands of the eyelid is the outermost layer of the tear film. Its main function is to increase the surface tension of the tear film, retard evaporative tear loss and provide lubrication between the lids and the ocular surface.

Water (Aqueous) Layer:

This layer produced by the lacrimal gland is the middle layer of the tear film and accounted for most of the tear film. The water layer contains nutrients, vitamins and antibiotics. Its main function is to provide a clear and lubricated eye surface, supply oxygen to cornea and to wash away foreign bodies.

Mucin Layer:

This layer produced by the conjunctival goblet cells is the innermost layer of the tear film. Its main function is to ensure that the tear film can adhere to the ocular surface, provide a hydrophilic layer on the eye and allow for even distribution of the tear film.

Deficiency or uneven distribution for any of these three layers of the tear film could cause dry eye symptoms.

Xerophthalmia is a chronic disease that cannot be cured but the symptoms can be treated. The current treatment of xerophthalmia consists of medical and surgical therapies:

Medical Therapies of Xerophthalmia

1. Artificial tears: The function of artificial tears comprises wetting eyes, diluting inflammatory substances and reducing tear osmolarity, and therefore is the most common treatment for patients with xerophthalmia. If patients are allergic to preservatives or use artificial tears at a high frequency (above 4 to 6 times a day), it is recommended for patients to use preservative-free artificial tears to lubricate the eyes.

2. Autologous serum: The composition of serum proteins in tears resembles that of whole serum. Serum is rich in growth factors, and therefore can be used to treat patients with xerophthalmia as natural tear substitutes. The frozen serum can be preserved for 3 to 6 months, so the patients do not need frequent blood draws.

3. Mucolytics (mucus dissolving agents): They are medicines used to treat respiratory diseases. Mucolytics can reduce tear secretion decrease tear volume and lyse mucous plaques on the ocular surface.

4. Lacrisert: This medication is a solid artificial tear that is placed into the deepest section of lower eyelid to treat dry eyes. It works by maintaining lubrication and keeping the eye moist within 24 hrs. The disadvantage of lacrisert is that it is hard to install, and it might slightly affect patients' vision.

5. Anti-inflammatory therapy: In addition to deficiency of tears, ocular inflammation is also an important cause of xerophthalmia. Thus, use of topical steroids or Restasis (cyclosporine ophthalmic emulsion) is another treatment method. Restasis was approved by the FDA in 2002 as the only therapeutic treatment to increase tear production in patients with chronic dry eyes.

6. Antibiotics: Oral antibiotics, particularly tetracycline or doxycycline, are effective treatments for eyelid inflammation, especially for patients with rosacea. These patients treated with oral antibiotics should practice frequent eyelid hygiene and apply warm compresses. Moreover, topical vitamin A creams is another treatment option. The cream can be used before sleep but its effect is still controversial.

7. If patients have an autoimmune disease, they should also refer to a rheumatologist for evaluation.

Surgical Therapies of Xerophthalmia

Surgical therapies are generally used for patients with severe dry eyes or when medical treatments have proven ineffective. Common surgical therapies are as follows:

1. Punctal plugs: This method blocks the lacrimal canaliculi to conserve the tears so that most of tears can stay on the ocular surface and stable the tear film. In general, the ophthalmologist will use absorbable inserts to tamponade at first. If this operation can reduce the symptoms of xerophthalmia, a permanent plug will be considered. If a punctal plug is to be used, patients must pay attention to inflammation as it can cause ocular surface damages.

2. Tarsorrhaphy: Patients suffering from severe dry eye, corneal ulcers, or Bell's palsy may perform Tarsorrhaphy to help protect the eye until the underlying condition can be corrected.

Diagnosis of Xerophthalmia

Diagnosis of xerophthalmia should be performed by a qualified physician. The diagnosis method includes interviews, physical examination and/or standardized tests such as Schirmer's test, corneal and conjunctival staining test, and fluorescein tear film break-up time test.

*Cordyceps cicadae* (*C. cicadae*)

Description and Distribution

*Cordyceps cicadae*, also known as tǔ chán huā, Chong hua, chan cao, hu chan, chan jun, chan yong cao, jin chan hua, chan rong and can rong, is a division of Ascomycotina, order of Claricipiyales, family of Clavicipitaceae and genus of *Cordyceps* fungi. *Cordyceps* species are insect-fungus complexes that strictly parasitize on the larva of *Cicada flammate, Platypleura kaempferi, Crytotympana pustulata, Platylomia pieli*, and many more. *C. cicadae, C. sobolifera* and *C. cicadicola* are the most common types of *Cordyceps* and are classified based on the hosts in which they reside. The genus is mainly distributed in subtropical and tropical region such as south Yangtze River, i.e. Fujian, Zhejiang, Sichuan, Yunnan and Jiangsu in China. The genus is also distributed in some mountains in Taiwan.

The sexual stage of *Paecilomyces cicadae* is called *C. cicadae*, also known as du jiao long.

Potential pharmacology of *C. cicadae*

*C. cicadae* have a long history of use in traditional medicine. In *Herbology of classified syndromes* documented by Shen-wei Tang in the Northern Song Dynasty, it was written that *C. cicadae* is sweet in flavor, cold in nature and nontoxic, which can dispel wind and heat from the body, relieve convulsion and spasm. It is intended for morbid night crying of babies and palpitation (Compendium of Materia Medica).

*C. cicadae* had been used as a medicine for about 1,500 years in China, which was 800 years longer than *C. sinensis*. *C. cicadae* was introduced to central China from Tibet in Qing Dynasty, and was recorded in the ancient scriptures of material medica as a chinese materia medica. The term of *C. cicadae* was first mentioned in the Process Analysis about Tripterygium written by Xiao Lei in the Liu Song Period of Northern and Southern Dynasties. In this book, it is recorded that *C. cicadae* with contact white flower should be used, and coating mud should be removed before boiling overnight. The next day, it is dried and grinded into powder.

It was recorded in classic medical work of *Collections of the herbs* compiled by Su song in the Song Dynasty that horn-like (or antler-like) protuberances occurred on the heads of *Cicada* in mountain, which is called *C. cicadae*. *Compendium of Materia Medica* said "The effectiveness of chán huā is similar to that of *Cicada* slough, which could cure malaria." However, no one has yet produced such evidence.

Many tradition medicine products comprise of *C. cicadae* called "wan ying chan hua san", "chan hua ming mu fang" and "chan hua wu wei san" have been documented in (*Index of Chinese medicine*) and (Zhōng huá yào hǎi).

A previous study has showed that among the patients subjected to therapy project of combining "chan hua wu wei san" and western medicine, 14 subjects of which achieved a normal intraocular pressure (>1.33 kPa), with a response rate of 46.67%. However, among 30 patients underwent western medicine treatment group, 8 patients achieved a normal intraocular pressure, with an average intraocular pressure of 0.41 kPa and a response rate of 26.67% (1994, Guang-hua Peng). Furthermore, the clinical trials conducted in 100 patients diagnosed with vernal conjunctivitis revealed that "wan ying chan hua san" could alleviate conjunctival congestion and reduce the incidence of relapse. The response rates was 78% in the treatment group, whereas, only 26% in the control group. The 1-year recurrence rate was 22% and 88%, respectively.

Both *C. cicadae* and *C. sinensis* are fungus-insect complexes with similar composition. Thus, *C. cicadae* is often viewed as a substitute of *C. sinensis*. As the wild *C. sinensis* resources are decreasing every year, artificial culture of *C. cicadae* received great attention as a promising alternative for efficient production. Since the production of wild *C. cicadae* is particularly affected by climate or human factors, using artificial cultured *C. cicadae* to replace the wild ones is therefore a good idea. Due to its high economic value, many researchers have cultivated the *C. cicadae* mycelium by liquid culture.

SUMMARY

The present invention provides *Cordyceps cicadae* (*C. cicadae*) mycelium active substances, preparation method, and the application for treating/preventing corneal injury or xerophthalmia induced by physical or chemical damages. Compared to general treatments of xerophthalmia (medicine or eye drops), the present invention provides a much safer, easier way to prevent or treat this disease. The *C. cicadae* mycelium active substances of present invention are natural and are safer than other drugs.

According to one embodiment of the present invention, a method for preparation a *C. cicadae* mycelium active substances is provided. The *C. cicadae* mycelium active substances are for preventing and/or treating xerophthalmia. The method comprises the following steps:

(a) culturing a *C. cicadae* mycelium in a plate media at 15 to 35° C. for 5 to 14 days;

(b) inoculating the *C. cicadae* mycelium of step (a) to a flask containing liquid media and culturing the mycelium at 15 to 35° C. with a pH of 2 to 8 for few days;

(c) inoculating the *C. cicadae* mycelium of step (b) to a fermenter tank and culturing the mycelium at 15 to 35° C. with a pH of 2 to 8 for 3 days, so as to obtain a *C. cicadae* mycelium fermentation liquid;

(d) freeze-drying and grating the *C. cicadae* mycelium fermentation liquid, so as to obtain a *C. cicadae* mycelium powder;

(e) extracting the *C. cicadae* mycelium powder with at least one solvent, so as to obtain *C. cicadae* mycelium extract; and (f) drying the *C. cicadae* mycelium extract, so as to obtained the *C. cicadae* mycelium active substances.

In one embodiment of present invention, the culturing process of above step (b) is shake flask cultivation, and the flask is shaking at a speed range between 10 and 250 rpm.

In one embodiment, the gas feed in the fermenter tank in step (c) comprises air, oxygen, carbon dioxide, helium or a combination thereof.

In one embodiment, the pressure of the fermenter tank in step (c) is at 0.5 to 1.0 $kg/cm^2$, and the gas flow rate of fermenter tank is 0.01 to 1.5 VVM.

In one embodiment, the liquid media used in step (b) and step (c) are the same. The liquid media comprises grains, beans, inorganic salts, carbohydrates, yeast extract, malt extract or a combination thereof.

In one embodiment, the solvent of step (e) comprises water and alcohol.

In one embodiment, the extracting process of step (e) uses two solvents, which comprise water and alcohol.

In one embodiment, the alcohol of step (e) is methanol or ethanol.

In one embodiment of step (f), water extracts and alcohol extracts from the *C. cicadae* mycelium powder are mixed to obtain the *C. cicadae* mycelium active substances.

In one embodiment, the *C. cicadae* mycelium active substances comprise the same weight of water extracts and alcohol extracts from the *C. cicadae* mycelium powder.

According to another embodiment of present invention, a *C. cicadae* mycelium active substances made by foregoing method is provided.

According to another embodiment of present invention, a method for preventing and/or treating xerophthalmia is provided. The method comprises administrating to a subject an effective amount of the above-mentioned *C. cicadae* mycelium active substances.

According to another embodiment of the present invention, a pharmaceutical composition for preventing and/or treating xerophthalmia is provided. The pharmaceutical composition comprises a therapeutically effective amount of above *C. cicadae* mycelium active substances in admixture with a pharmaceutically acceptable carrier, excipient, diluents or adjuvant.

According to another embodiment of present invention, a method for preventing and/or treating xerophthalmia is provided. The method comprises the pharmaceutical composition of claim.

Many of the attendant features and advantages of the present invention will becomes better understood with reference to the following detailed description considered in connection with the accompanying drawings.

BRIEF DESCRIPTION OF THE DRAWINGS

FIG. 1A illustrates the related tear change ratio of UVB mice; FIG. 1B illustrates the related tear change ratio of BAC mice; FIG. 1C illustrates the tear production of UVB mice; FIG. 1D illustrates the tear production of BAC mice.

FIG. 2A illustrates the average level of cornea smoothness of UVB mice; FIG. 2B illustrates the average level of cornea smoothness of BAC mice.

FIG. 3A illustrates the average level of cornea opacity of UVB mice; FIG. 3B illustrates the average level of cornea opacity of BAC mice.

FIG. 4A illustrates the average level of corneal topography of UVB mice; FIG. 4B illustrates the average level of corneal topography of BAC mice.

FIG. 5A illustrates the average level of cornea staining of UVB mice; FIG. 5B illustrates the average level of cornea staining of BAC mice.

FIG. 6A is the corneal H-E stain of UVB mice; FIG. 6B is the corneal H-E stain of BAC mice.

FIG. 7A illustrates the tear film breakup time of UVB mice; FIG. 7B illustrates the tear film breakup time of BAC mice; FIG. 7C illustrates the relative tear film breakup time of UVB mice; FIG. 7D illustrates the relative tear film breakup time of BAC mice.

FIG. 8A illustrates the average level of corneal sensitivity of UVB mice; FIG. 8B illustrates the average level of corneal sensitivity of BAC mice.

DETAILED DESCRIPTION

Principles

Figure 1A:
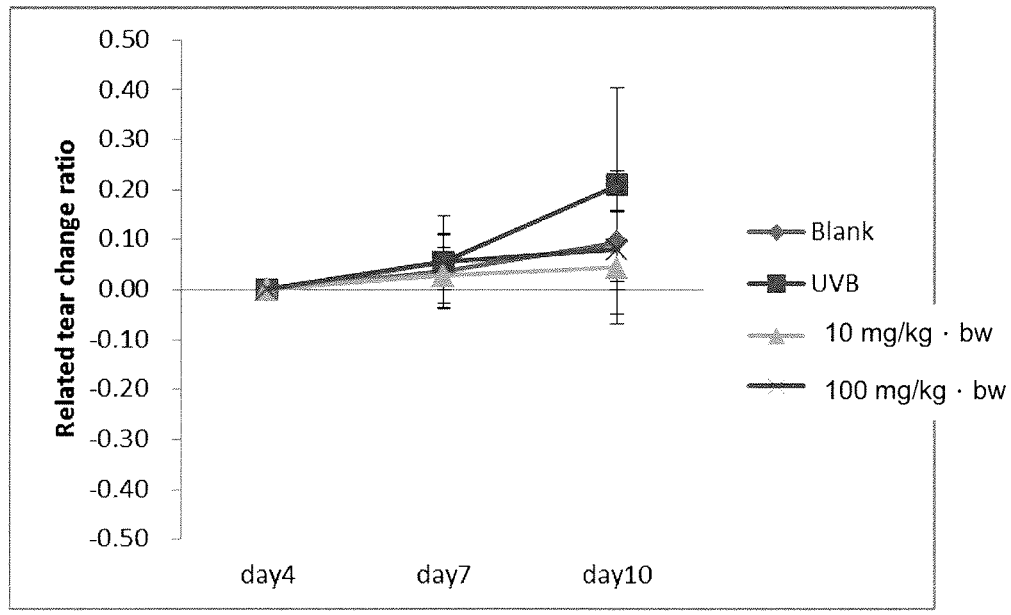
FIG. 1A to FIG. 1D show the test results of tear production in mice (corresponding with Table 3-1 to Table 3-4).

The cornea is one the most sensitive tissue in human body, as it is densely innervated with sensory nerve fibers. The cornea is located in the front portion of eye, is in direct contact with the air, contains no vascular tissue, obtains nutrients and oxygen from tears and aqueous humor, and is easily infected. Embodiments of the present invention use a physical or chemical method to induce corneal injuries, and evaluate the effects of *Cordyceps cicadae* mycelium active substances on preventing and/or treating eye diseases caused by corneal injuries (such as Xerophthalmia).

Ultraviolet (UV) can be divided into three types by wavelength: UVA (315-380 nm), UVB (280-315 nm) and UVC (100-280 nm). Excessive exposure to ultraviolet radiation (especially for UVB) can cause photochemical damage to the eye. UV may induce formation of free radicals, and thus inactivates the antioxidant enzyme activity in the cornea. UVB rays are absorbed by the cornea, and can cause ocular surface disorders, corneal injury, conjunctival connective tissue proliferation, keratinocyte hyperplasia, and can accelerate the aging process of the eye and the tissue around the eye. Ongoing exposure to UVB can cause pain and foreign body sensation in the eye, corneal inflammation, epithelial desquamated and degenerative cornea. Sunglasses are used to protect the eyes from the sun, but the public seldom think to protect their eyes. The public usually ignores the damage, resulting in decreased tear production and increased risk of xerophthalmia.

Benzalkonium chloride (BAC, BAK) is a cationic surfactant (non-oxidizing antiseptic) for sterilization, disinfection, antisepsis, emulsification, detergency, solubilization, etc. BAC was added in eye drops as a preservative, but recent research has shown that this compound may cause tear film instability, loss of goblet cells, conjunctival squamous metaplasia and apoptosis, corneal epithelium or eye tissues injury. Mild symptoms of eye injury include inflammation and xerophthalmia, and severe symptoms include permanent injury to the ocular surface and might affect vision. The reason why BAC causes above effects has not yet been clarified, but current research confirmed that BAC induces release of proinflammatory cytokine, apoptosis and oxidative stress, which can lead to dysregulated immune reactions and thereby cause chronic inflammatory. In addition, BAC can cause detrimental effect on the tear film stability and corneal surface integrity by direct interaction with the lipid bilayer.

Based on the above principles, the present invention designs two animal models (UVB and BAC mice) to observe the application of *C. cicadae* mycelium active substances on preventing and/or treating xerophthalmia induced by physical or chemical damages.

Experimental Methods
Preparation of *C. cicadae* Mycelium Active Substances

Source of *Cordyceps cicadae* Mycelium

*Cordyceps cicadae* (*C. cicadae*) mycelium in embodiments of present invention is obtained by following steps: gathering a natural Taiwanese *C. cicadae* strain, separating its mycelium and storing the subculture on the plate media. The gene sequence of strain is confirmed as *C. cicadae* by Taiwan Food Industry Research and Development Institute. This strain has been deposited in public repository (Bioresource Collection and Research Center, BCRC; China General Microbiological Culture Collection Center, CGMCC) and the Storage No. are MU30106 (BCRC) and 10486 (CGMCC). However, it is noted that the *C. cicadae* active substances of present invention are not limited to any particular species but widely include those known in the art.

Liquid Culture

*C. cicadae* mycelium and *C. cicadae* mycelium active substances was established by growing its mycelium on the plate media at 15 to 35° C. (preferably 25° C.) for 5 days to 2 weeks, and then the mycelium was inoculated into a flask containing liquid media. The above mycelium is cultured in the flask at 15-35° C. (preferably 25° C.), pH 2-8 (preferably pH 4-7, more preferably pH 4.5) and shake at a rate below 10-250 rpm for about 3 days. The culture time may be adjusted depending on the environment and growth of mycelium. Then the mycelium is further transferred to a fermenter tank (the media in the fermenter tank is shown in Table 1, and is the same liquid media used in the flask). The condition in the fermenter tank is set to a temperature of 15-35° C. (preferably 25° C.), a pressure of 0.5-1.0 kg/cm$^2$, a pH of 2-8, a stirring rate of 10-150 rpm (or air lift), and an air flow rate of 0.01-1.5 VVM (air could be replace by air, oxygen, carbon dioxide, helium or combination thereof, preferably air) for 3 to 5 days to obtain *C. cicadae* mycelium fermentation liquid. The fermentation liquid comprises mycelium, supernatant, and the *C. cicadae* mycelium active substances of the present invention. The *C. cicadae* mycelium fermentation liquid could also be dried to form powder.

TABLE 1

Recipe of media

| Ingredient | Amount (weight %) |
| --- | --- |
| Carbon and Nitrogen sources | 0.01~5 |
| Proteins and their hydrolysates | 0.01~2 |
| Yeast or malt extract (powder, cream) | 0.001~2 |
| Inorganic salts | 0.0001~0.05 |
| Carbohydrate | 0.01~10 |

In the above ingredient, carbon and nitrogen sources may be cereals (grains) or legumes (such as soya bean, mung bean or *Glycine max*); inorganic salts may be magnesium sulfate, dipotassium phosphate, monopotassium phosphate, ferric sulfate, etc.; carbohydrate may be glucose, fructose, maltose, sucrose, etc. It is noted that the above recipe of the media is just an example. The actual recipe of media may adjusted if necessity. Alternatively, the commercial media could be used.

Drying

The drying method may includes (but not limited to): spray drying, hot air drying, drum drying, freeze drying, concentration, etc. The fermentation liquid is dried to form powder.

Extraction

The drying fermentation liquid powder (*C. cicadae* mycelium powder) are divided into two independent parts. One part is for water extraction, and the other part is for alcohol extraction. 1. Water extraction Dissolve the drying fermentation liquid powder in water and heat the solution at 90-121° C. for few minutes. After cooling, dry the solution by one of the above drying methods (i.e. rotary evaporator) so as to obtain the water extract of the *C. cicadae* mycelium.

2. Alcohol Extraction

Dissolve another drying fermentation liquid powder (different part from that for water extraction) in alcohol solvents (1-100 weight or volume percentage of methanol or ethanol), stir the solution for few minutes, and dry the solution by one of the above drying method (i.e. rotary evaporator) so as to obtain alcohol extract of *C. cicadae* mycelium.

3. Extracts Mixture (in any Proportion)

The water extract and the alcohol extract of *C. cicadae* mycelium could be mixed in any proportion, and the present invention is not limited thereto.

Example 1 Liquid Culture and Preparation of *C. cicadae* Mycelium Active Substances

*Cordyceps cicadae* Mycelium:

Grow *C. cicadae* mycelium on plate media (Potato Dextrose Agar, PDA) at 25° C. for about 5 days.

Liquid Culture in a Flask:

Inoculate the mycelium from the plate to a flask containing media at pH 4.5, and incubate on a shaker (120 rpm) at 25° C. for 3 days (the recipe of flask media is shown in Table 2).

TABLE 2

Recipe of flask media

| Ingredient | Amount (weight %) |
| --- | --- |
| Sucrose | 2.0 |
| Yeast extract | 0.5 |
| Bean flour | 1.0 |

Liquid Culture in a Fermenter Tank:

The liquid media of fermenter is similar to that of the flask media (Table 2). The flask culture was inoculated to a fermenter tank at a pressure of 0.5 to 1.0 kg/cm$^2$, an air flow rate of 0.01 to 1.5 VVM, about 25° C., pH 4.5 and a stirring speed of 10-150 rpm or air lift for 3 days. The obtained mycelium and supernatant are called fermentation liquid. The fermentation liquid includes the active substances of the present invention. Freeze-drying the fermentation liquid can obtain the powder. The powder is divided into two independent parts for water and alcohol extraction.

Preparation of Extracts:

Water Extraction

Dissolve the powder in 20 times volume of distilled water and heat the solution at 100° C. for 30 minutes. After cooling, dry the solution by freeze-drying so as to obtain water extract of *C. cicadae* mycelium.

Alcohol Extraction

Dissolve the powder in 20 times volume of ethanol and place the solution in an ultrasonic bath for 30 minutes. The solution is then centrifuge and the supernatant is concentrated to obtain alcohol extract of *C. cicadae* mycelium.

The Extract Mixture

Mix the above mentioned water and alcohol extract of *C. cicadae* mycelium in the same weight, and then freeze-dry the mixture to obtain a water/alcohol extract mixture.

Results:

20 metric tons of *C. cicadae* mycelium fermentation liquid could be dried to about 110 kg freeze-dried powder. After extraction process, a higher yield of *C. cicadae* mycelium active substances is obtained for preventing/treating xerophthalmia induced by physical or chemical damages. The *C. cicadae* mycelium active substances exist in the fermentation liquid (mycelium and supernatant), the freeze-dried powder, the water/alcohol extract mixture, etc. of the present embodiment. The following Example 2 uses water/alcohol extract mixture as *C. cicadae* mycelium active substances.

Example 2 Xerophthalmia Animal Model and Analysis

1. Establishment of a Mice Animal Model of Xerophthalmia
Experimental Animals:

Female mice at 7 to 10 weeks of age weighed 25 to 33 g (ICR strain) were purchased from BioLASCO Taiwan and maintained in Chung Shan Medical University Laboratory Animal Center on a 12-h light/dark cycle in constant temperature and humidity. Mice were given food and water ad libitum during the whole experiment.

(1) Xerophthalmia Induced by Physical Damages Using a UV Lamp (UVB)

A UV lamp is bought from Vilber lourmat (model: VL-6MC). The wavelength is set to 280 nm~320 nm, and the main peak is at 312 nm.

Before the test, the mice were randomly divided into four groups of six: a blank control group (fed saline without UVB radiation), a UVB group (fed saline with UVB radiation), a low-dose group (fed 10 mg/kg·bw *C. cicadae* mycelium active substances with UVB radiation) and a high-dose group (fed 100 mg/kg·bw *C. cicadae* mycelium active substances, with UVB radiation)

The entire experiment was carried out for 10 days. For 10 days, the experimental groups (low- and high-dose groups) were fed with the predetermined doses of *C. cicadae* mycelium active substances (water/alcohol extract mixture) daily. From the 4th day to the end of the experiment, the mice of the UVB and the experimental groups were anesthetized with 2.5% Avertin, placed in a black box, and irradiated with 0.72 J/cm$^2$ UVB for 90 seconds to induce a dry eye condition. UVB-induced changes in tear production, tear film break-up time, corneal sensitivity, corneal surface damage parameters and tissue sections were evaluated to determine the effectiveness of *C. cicadae* mycelium active substances for treating/preventing xerophthalmia. The data shows (described in details later) that the *C. cicadae* mycelium active substances are effective to xerophthalmia induced by UVB.

(2) Xerophthalmia Induced by Chemical Damages Using BAC

Before the test, the mice were randomly divided into four groups of six: a blank control group (fed saline without BAC treatment), BAC group (fed saline with BAC treatment), a low-dose group (fed 10 mg/kg·bw *C. cicadae* mycelium active substances, with BAC treatment) and a high-dose group (fed 100 mg/kg·bw *C. cicadae* mycelium active substances, with BAC treatment)

The entire experiment was carried out for 14 days. For 14 days, the experimental groups (low- and high-dose groups) were fed the predetermined doses of *C. cicadae* mycelium active substances (water/alcohol extract mixture). From the 4th day to the end of the experiment, 5 μl of 0.2% BAC was dropped on the eyes of the mice of the BAC and experimental groups to induce a dry eye condition. BAC-induced changes in tear production, tear film break-up time, corneal sensitivity, corneal surface damage parameters and tissue sections were evaluated to determine the effectiveness of the *C. cicadae* mycelium active substances for treating/preventing xerophthalmia. The data shows (described in details later) that the *C. cicadae* mycelium active substances is effective to xerophthalmia induced by BAC.

2. Assessments of Ocular Surface Damage for Xerophthalmia

This experiment uses two types of mice animal models (UVB and BAC) to observe the effectiveness of the *C. cicadae* mycelium active substances for protecting/treating xerophthalmia. The ocular surface damage level and assessment for xerophthalmia were measured during the experiment and at the end of experiment.

The assessments for xerophthalmia is similar to that of a clinical xerophthalmia diagnosis, which includes a tear production test, a corneal surface damage test, a H&E staining test, a tear film breakup time and a corneal sensitivity test. The corneal surface damage test includes assessment for corneal smoothness, corneal opacity, corneal topography and corneal staining.

(1) Tear Production Test

The tear production test measures the basic tear production. This test uses litmus paper strips to measure the production of tears. The paper strip is inserted into the lower eyelid of mice eye for few seconds. The paper is then removed and the amount of moisture is measured.

(2) Corneal Surface Damage Analysis

The analysis includes assessments for corneal smoothness, corneal opacity, corneal topography and corneal staining. The higher the level indicates a more severe damage to the cornea.

(2.1) Corneal smoothness was evaluated by the regularity of the ring light reflected off the wet cornea. The result is grade to level 0-5: level 0 indicates the reflect light is annular without distortion; level 1-3 indicate ¼, ½, and ¾ of ring portion are distorted, respectively; level 4 indicates the whole ring light is distorted; level 5 indicates the light is extremely distorted thus cannot be recognized as a ring.

(2.2) Corneal opacity was evaluated by lighting the eyes. The result is graded to 4 levels by transparency. Level 1 indicates normal corneal transparency; Level 1-3 indicate mild, moderate, moderate (with unclear iris) opaque degeneration; Level 4 indicates severe opaque degeneration, i.e. white turbidity and corneal ulceration.

(2.3) Corneal topography was evaluated by projecting quintuple ring graph on the ocular surface. The assessment of corneal topography is to divide the ocular surface into four areas, each with 5 arc lines (from the projected quintuple rings). If any of the arc line is twisted or unreadable, score 1 point. A total of 20 points was scored on each eye. The higher the point, the lower the smoothness of cornea. The result is graded to level 0-5. Level 1 is 0 point; Level 1 is 1-4 points; Level 2 is 5-9 points; Level 3 is 10-14 points; Level 4 is 15-19 points and Level 5 is 20 points.

(2.4) Corneal staining was evaluated by scoring fluorescein staining under a hand-held slit lamp. The size of stain is graded to level 0-5. Level 0 is without punctate staining; Level 1 indicates 25% or less area with scattered punctuate staining; Level 2 indicates 25-50% area with diffuse punctate staining; Level 3 indicates 50-75% area with diffuse punctate staining; Level 4 indicates 75%-99% area with abundant punctate staining, Level 5 indicates the entire cornea is stained.

(3) Hematoxylin and Eosin Stain (H & E Stain)

This is one of the most common histological staining methods. Hemalum colors nuclei of cells while eosin colors cytoplasm and extracellular matrix in red. After the end of experiment, the mice were sacrificed. The eye tissues of the mice were soaked in 3% formalin and dehydrated by n-butanol. The H&E test was performed to observe the cell layers, patterns and the thickness of central cornea, thereby evaluating the effectiveness of the *C. cicadae* mycelium active substances.

(4) Tear Film Break-Up Time (TBUT)

Tear film quality is one of factors causing xerophthalmia. A tear film break-up time indicates the stability of the tear film and can be used to evaluate the quality of the tear. 1 μL of 0.1% sodium fluorescein solution was dropped on the bulbar conjunctiva of the mice and the tear film break-up time was recorded after three blinks. 90 seconds later, the extent of cornea injury was evaluated by a microscope. The cornea is divided into four quadrants (each quadrant has 4 points) and is individually scored. 0 point indicates unstained; 1 point indicates slightly stained but less than 30 dots; 2 points indicate more than 30 staining dots but no diffusion; 3 points indicate severe staining and diffusion in the quadrant, but no significant plaques; 4 point indicates obvious fluorescent plaques.

(5) Corneal Sensitivity (CS)

This test uses Cochet and Bonnet aesthesiometer to measure the length of filament required to elicit a blink reflex. If mice have no blinking response, retract the filament until the mice blink. Four times with no blinking response can be recorded as "no response". In the absence of blink response, the filament length was reduced by 0.5 cm and the animal retested. The filament ranges from 6 cm to 0.5 cm (0.5 cm interval) and contacts the corneal surface in a perpendicular direction. The stimulus pressure applied is inversely proportional to the filament length. Blink with 0.5 cm filament contacts scores 0 point. Each test must be performed by the same operator.

The above results are analyzed with Mann-Whitney U test by SPSS (18th version). The asterisk (*) indicates a significant result with $p<0.05$.

Example 3 Assessment for Effectiveness of the *C. cicadae* Mycelium Active Substances for Preventing Xerophthalmia 1. Tear Production Test In this test, the litmus paper with 1 mm width (Toyo Roshi Kaisha, Ltd) was inserted into the lower eyelid of the mouse's eye. 20 seconds later, the paper is removed and the amount of moisture is measured. The result is shown in Table 3-1 to Table 3-4 (corresponding to FIGS. 1A to 1D). The result showed that *C. cicadae* mycelium active substances can increase the tear production and reduce the relative tear change ratio, thus is good for preventing xerophthalmia

TABLE 3-1

The related tear change ratio (mm) of UVB mice (Corresponding with FIG. 1A)

| Group | Day 4 | Day 7 | Day 10 |
|---|---|---|---|
| Blank | 0.00 | 0.04 | 0.09 |
| UVB | 0.00 | 0.06 | 0.21 |
| 10 mg/kg · bw | 0.00 | 0.03 | 0.04 |
| 100 mg/kg · bw | 0.00 | 0.06 | 0.08 |

TABLE 3-2

Figure 1B:
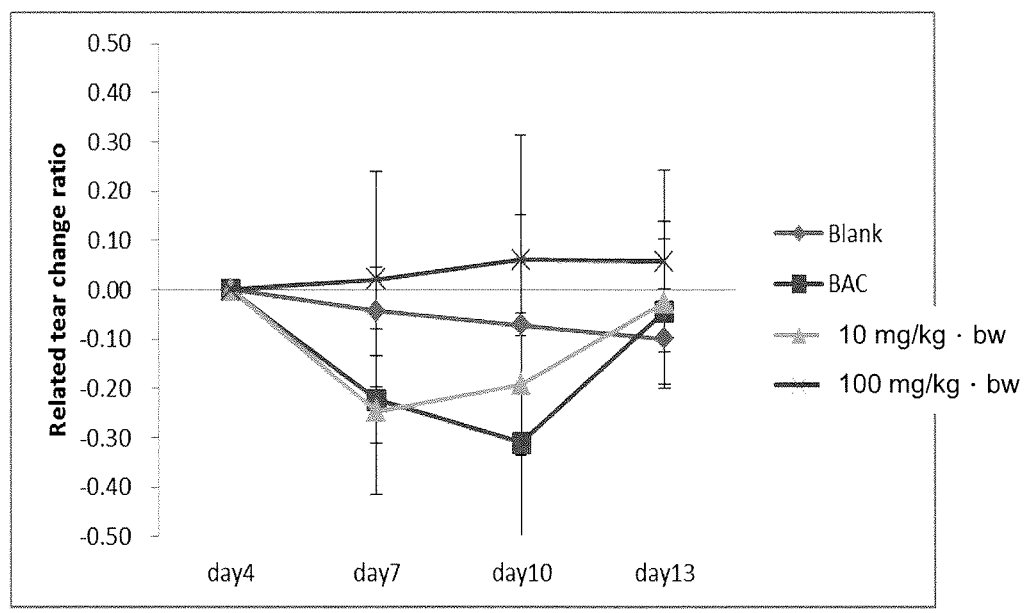

The related tear change ratio (mm) of BAC mice (Corresponding with FIG. 1B)

| Group | Day 4 | Day 7 | Day 10 | Day 13 |
|---|---|---|---|---|
| Blank | 0.00 | −0.04 | −0.07 | −0.10 |
| BAC | 0.00 | −0.22 | −0.31 | −0.04 |
| 10 mg/kg · bw | 0.00 | −0.25 | −0.19 | −0.03 |
| 100 mg/kg · bw | 0.00 | 0.02 | 0.06 | 0.06 |

TABLE 3-3

Figure 1C:
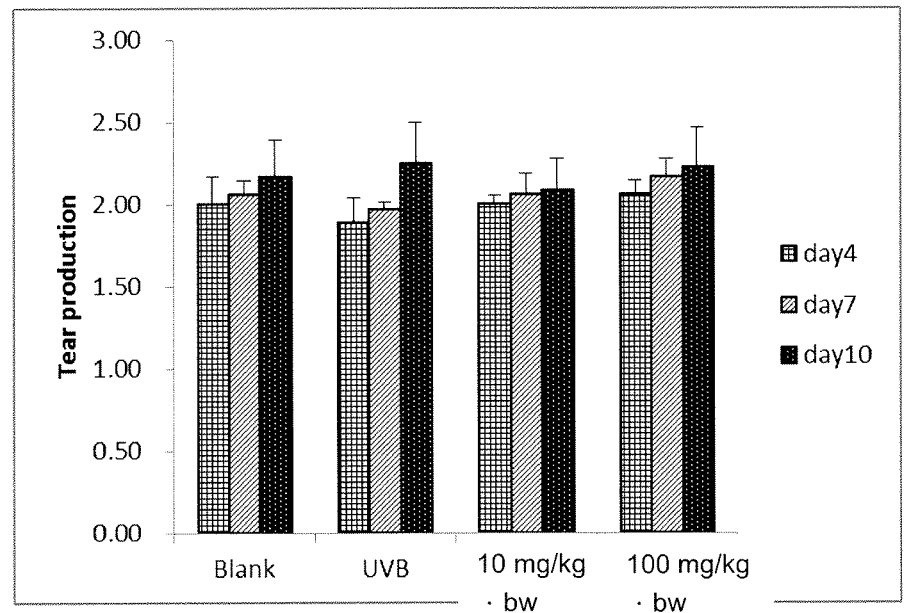

The tear production (mm) of UVB mice (Corresponding with FIG. 1C)

| Group | Day 4 | Day 7 | Day 10 |
|---|---|---|---|
| Blank | 2.00 | 2.06 | 2.17 |
| UVB | 1.89 | 1.97 | 2.25 |
| 10 mg/kg · bw | 2.00 | 2.06 | 2.08 |
| 100 mg/kg · bw | 2.06 | 2.17 | 2.22 |

TABLE 3-4

Figure 1D:
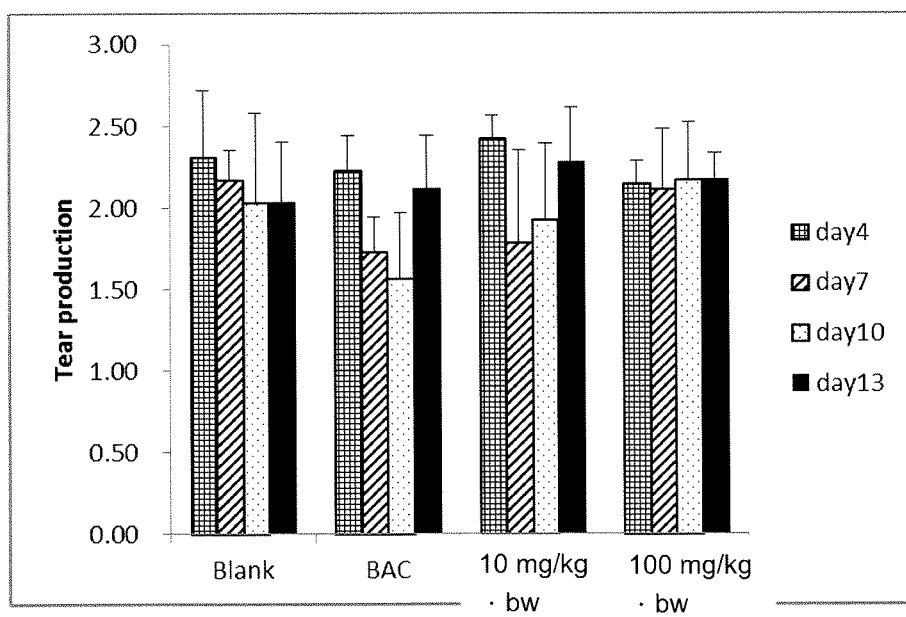

The tear production (mm) of BAC mice (Corresponding with FIG. 1D)

| Group | Day 4 | Day 7 | Day 10 | Day 13 |
|---|---|---|---|---|
| Blank | 2.31 | 2.17 | 2.03 | 2.03 |
| BAC | 2.22 | 1.72 | 1.56 | 2.11 |
| 10 mg/kg · bw | 2.42 | 1.78 | 1.92 | 2.28 |
| 100 mg/kg · bw | 2.14 | 2.11 | 2.17 | 2.17 |

2. Corneal Surface Damage Analysis (1) Corneal smoothness was evaluated by the regularity of the ring light reflected off the wet cornea. The integrity is grade to level 0 (without distort) to 5 (severe distort). The results are shown in Table 4-1 and Table 4-2 (corresponding to FIGS. 2A to 2B). The result shows the mice of experimental groups (feeding the *C. cicadae* mycelium active substances) have lower image distortion than those of the blank control group. Thus it is good for preventing Xerophthalmia

TABLE 4-1

Figure 2A:
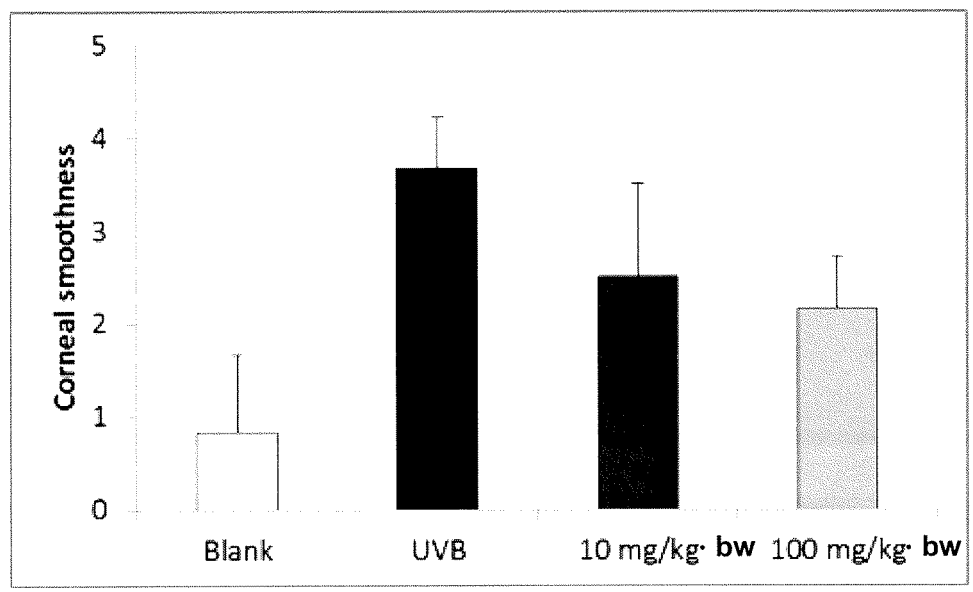
FIG. 2A and FIG. 2B show the test results of corneal smoothness in mice (corresponding with Table 4-1 and Table 4-2).

Average level of cornea smoothness of UVB mice (Corresponding with FIG. 2A)

| | Group | | | |
|---|---|---|---|---|
| Mouse | Blank | UVB | 10 mg/kg · bw | 100 mg/kg · bw |
| 1 | 2.0 | 4.0 | 1.0 | 2.0 |
| 2 | 2.0 | 4.0 | 2.0 | 3.0 |
| 3 | 0.0 | 4.0 | 4.0 | 3.0 |
| 4 | 0.0 | 4.0 | 2.0 | 2.0 |
| 5 | 0.0 | 2.0 | 4.0 | 1.0 |
| 6 | 1.0 | 4.0 | 2.0 | 2.0 |
| Avg. Level | 0.8 | 3.7 | 2.5 | 2.2 |

TABLE 4-2

Figure 2B:
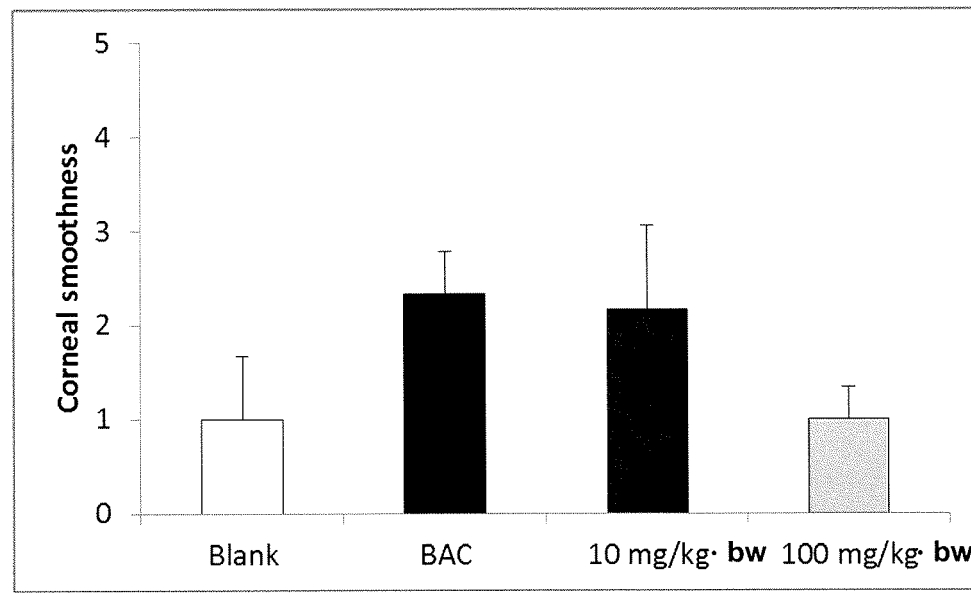

Average level of cornea smoothness of BAC mice
(Corresponding with FIG. 2B)

| Mouse | Group | | | |
|---|---|---|---|---|
| | Blank | BAC | 10 mg/kg · bw | 100 mg/kg · bw |
| 1 | 2.0 | 2.0 | 4.0 | 1.0 |
| 2 | 1.0 | 3.0 | 3.0 | 1.0 |
| 3 | 1.0 | 2.0 | 1.0 | 2.0 |
| 4 | 0.0 | 3.0 | 2.0 | 1.0 |
| 5 | 2.0 | 2.0 | 2.0 | 1.0 |
| 6 | 0.0 | 2.0 | 1.0 | 0.0 |
| Avg. Level | 1.0 | 2.3 | 2.2 | 1.0 |

(2) Corneal opacity was evaluated by lighting the eyes. The opacity is graded to 4 levels by transparency. The result is shown in Table 5-1 and 5-2 (corresponding with FIG. 3A and FIG. 3B). The result shows that in both BAC and UVB tests, the mice of experimental groups (feeding the *C. cicadae* mycelium active substances) have lower corneal opacity level than those of the blank control group, and the corneal opacity of mice are improve by the *C. cicadae* mycelium active substances. Thus it is good for preventing xerophthalmia

TABLE 5-1

Figure 3A:
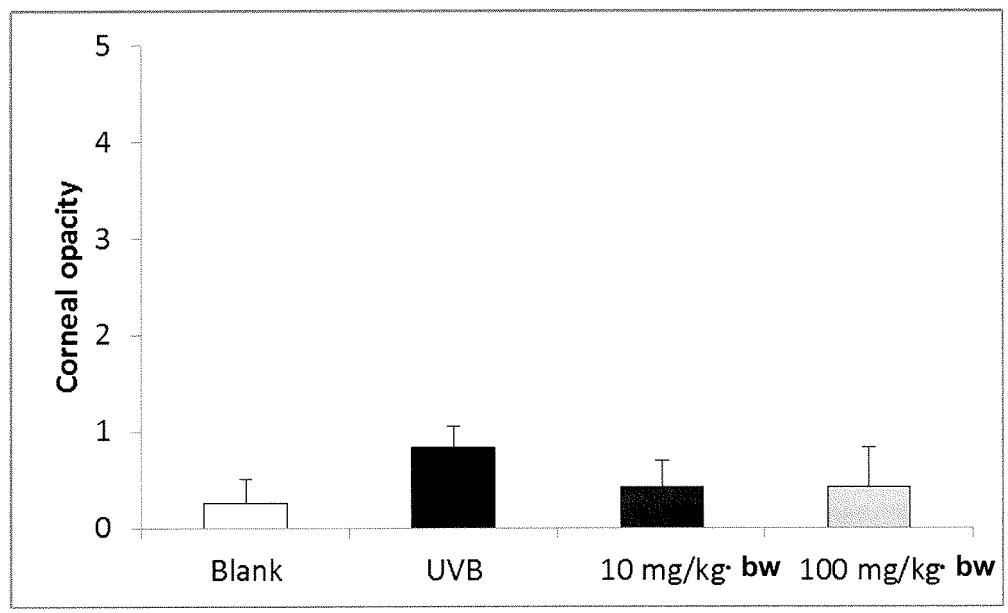
FIG. 3A and FIG. 3B shows the test results of corneal opacity in mice (corresponding with Table 5-1 and Table 5-2).

Average level of cornea opacity of UVB mice
(Corresponding with FIG. 3A)

| Mouse | Group | | | |
|---|---|---|---|---|
| | Blank | UVB | 10 mg/kg · bw | 100 mg/kg · bw |
| 1 | 0.5 | 0.5 | 1.0 | 1.0 |
| 2 | 0.5 | 1.0 | 0.5 | 0.0 |
| 3 | 0.0 | 1.0 | 0.5 | 0.5 |
| 4 | 0.0 | 1.0 | 0.0 | 1.0 |
| 5 | 0.0 | 0.5 | 0.5 | 0.0 |
| 6 | 0.5 | 1.0 | 0.0 | 0.0 |
| Avg. Level | 0.3 | 0.8 | 0.4 | 0.4 |

TABLE 5-2

Figure 3B:
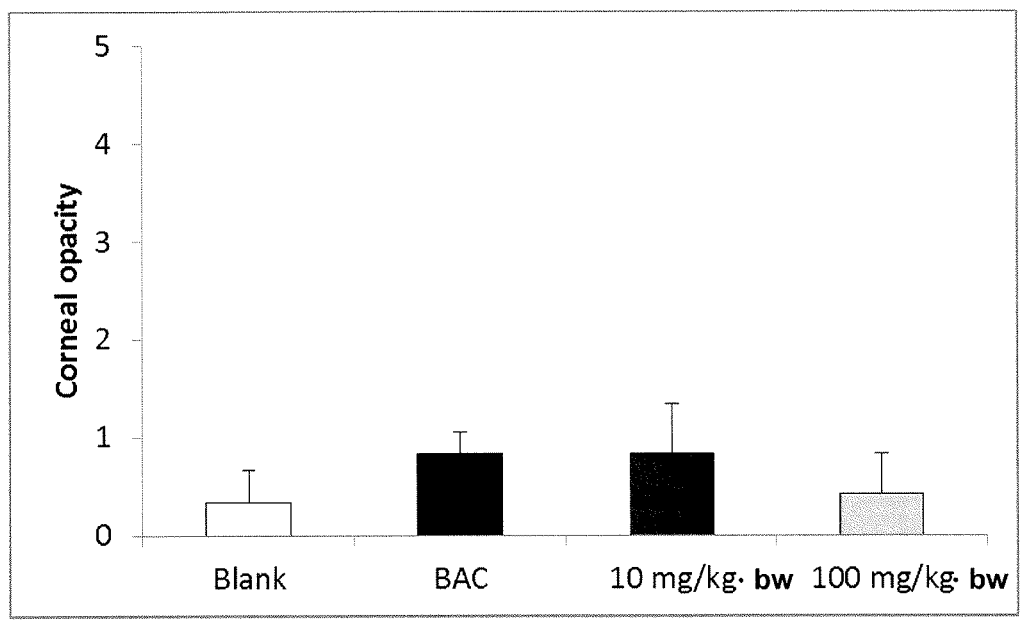

Average level of cornea opacity of BAC mice
(Corresponding with FIG. 3B)

| Mouse | Group | | | |
|---|---|---|---|---|
| | Blank | BAC | 10 mg/kg · bw | 100 mg/kg · bw |
| 1 | 0.0 | 1.0 | 2.0 | 0.5 |
| 2 | 0.0 | 1.0 | 1.0 | 0.0 |
| 3 | 0.5 | 1.0 | 1.0 | 1.0 |
| 4 | 0.5 | 0.5 | 0.5 | 0.0 |
| 5 | 0.0 | 1.0 | 0.5 | 1.0 |
| 6 | 1.0 | 0.5 | 0.0 | 0.0 |
| Avg. Level | 0.3 | 0.8 | 0.8 | 0.4 |

(3) Corneal topography was evaluated by projecting quintuple ring graph on the ocular surface. The assessment of corneal topography is divided the ocular surface into four areas, each area includes 5 arc lines (from the projected quintuple rings). If any of the arc line is twisted or unreadable, score 1 point. All eye score 20 points. The result is graded to level 0-5 and is shown in Table 6-1 and 6-2 (corresponding with FIG. 4A and FIG. 4B). The result shows that in both BAC and UVB tests, the mice of experimental groups (feeding the *C. cicadae* mycelium active substances) have lower ring distortion than those of the blank control group, and the corneal smoothness of mice are improve by the *C. cicadae* mycelium active substances. Thus it is good for preventing xerophthalmia.

TABLE 6-1

Figure 4A:
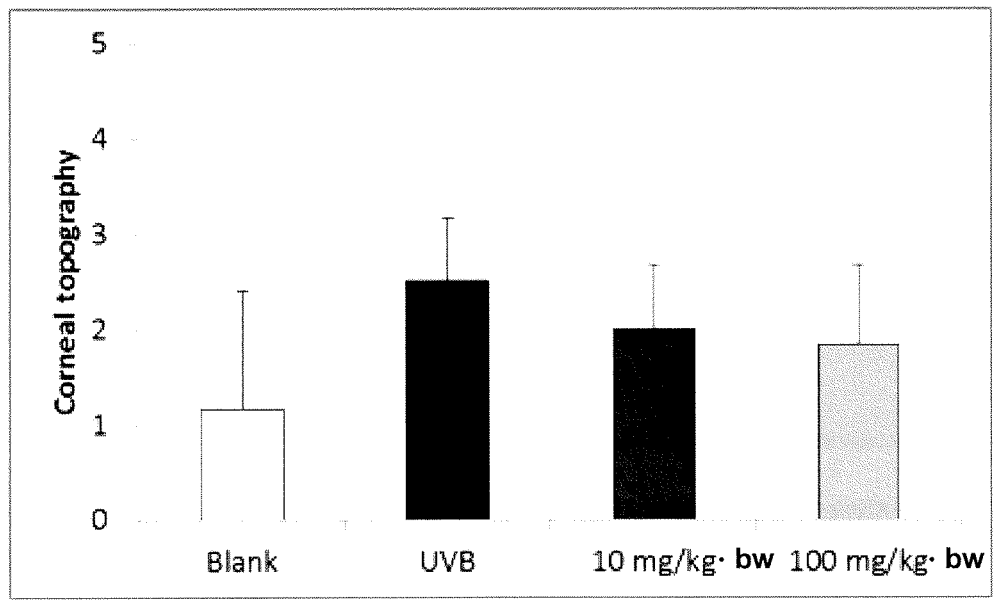
FIG. 4A and FIG. 4B show the test results of corneal topography in mice (corresponding with Table 6-1 and Table 6-2).

Average level of corneal topography of UVB mice
(Corresponding with FIG. 4A)

| Mouse | Group | | | |
|---|---|---|---|---|
| | Blank | UVB | 10 mg/kg · bw | 100 mg/kg · bw |
| 1 | 4.0 | 3.0 | 1.0 | 3.0 |
| 2 | 2.0 | 2.0 | 2.0 | 3.0 |
| 3 | 0.0 | 2.0 | 1.0 | 2.0 |
| 4 | 0.0 | 4.0 | 2.0 | 1.0 |
| 5 | 0.0 | 2.0 | 3.0 | 1.0 |
| 6 | 1.0 | 2.0 | 3.0 | 1.0 |
| Avg. Level | 1.2 | 2.5 | 2.0 | 1.8 |

TABLE 6-2

Figure 4B:
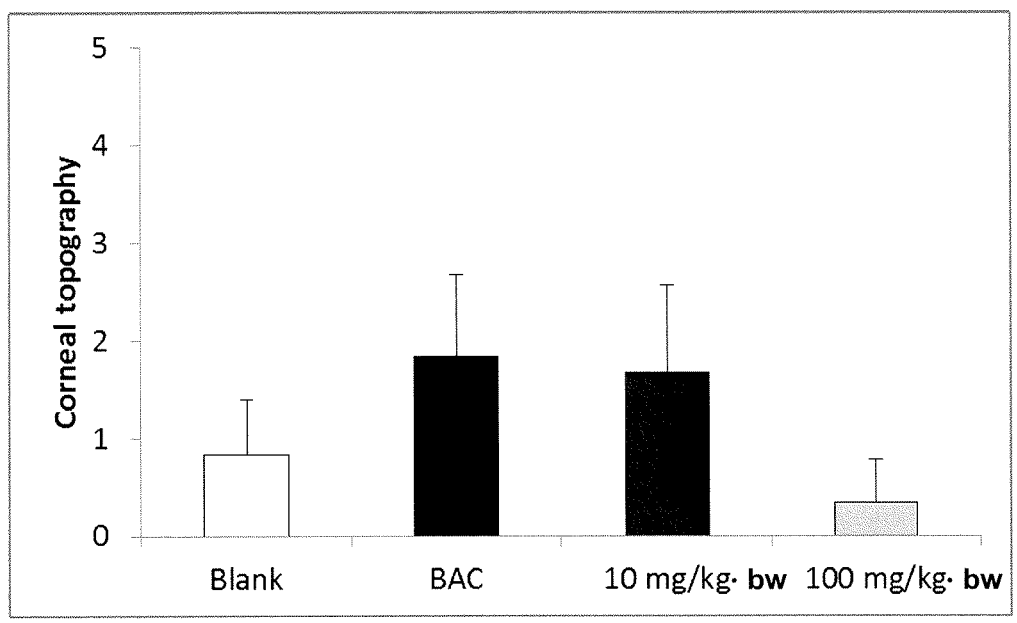

Average level of corneal topography of BAC mice
(Corresponding with FIG. 4B)

| Mouse | Group | | | |
|---|---|---|---|---|
| | Blank | BAC | 10 mg/kg · bw | 100 mg/kg · bw |
| 1 | 2.0 | 3.0 | 4.0 | 0.0 |
| 2 | 0.0 | 1.0 | 2.0 | 1.0 |
| 3 | 0.0 | 1.0 | 1.0 | 1.0 |
| 4 | 1.0 | 3.0 | 1.0 | 0.0 |
| 5 | 1.0 | 1.0 | 1.0 | 0.0 |
| 6 | 1.0 | 2.0 | 1.0 | 0.0 |
| Avg. Level | 0.8 | 1.8 | 1.7 | 0.3 |

(4) Corneal staining was evaluated by scoring fluorescein staining under a hand-held slit lamp. The size of stain is graded to level 0-5. The result is shown in Table 7-1 to 7-2 (corresponding to FIG. 5A to FIG. 5D). The result shows that in both BAC and UVB tests, the mice of experimental groups (feeding the *C. cicadae* active substances) have lower staining area than those of the blank control group, thus is good for preventing xerophthalmia

TABLE 7-1

Figure 5A:
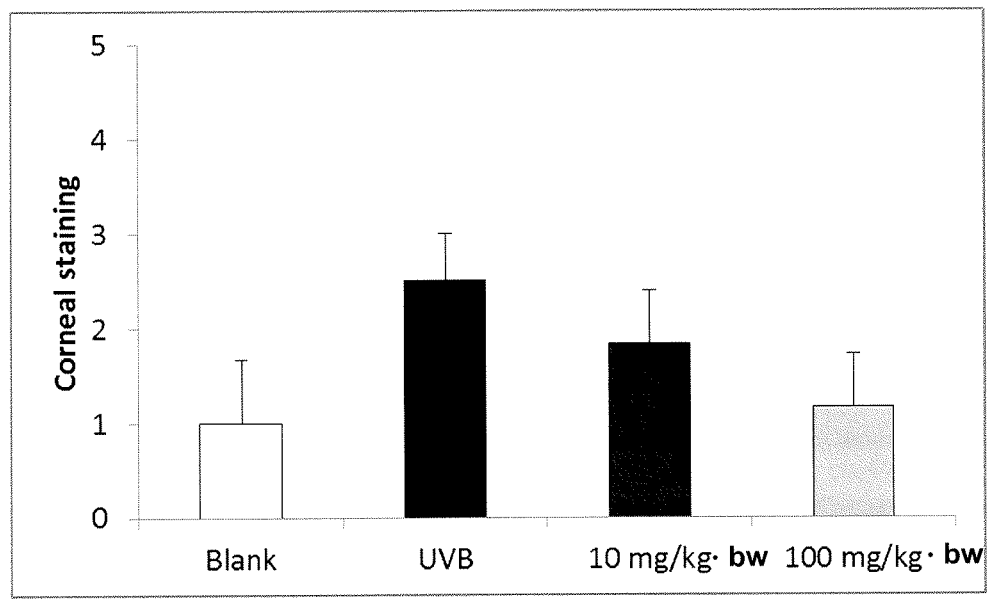
FIG. 5A and FIG. 5B show the test results of corneal staining in mice (corresponding with Table 7-1 and Table 7-2).

Average level of corneal staining of UVB mice
(Corresponding with FIG. 5A)

| Mouse | Group | | | |
|---|---|---|---|---|
| | Blank | UVB | 10 mg/kg · bw | 100 mg/kg · bw |
| 1 | 2.0 | 3.0 | 1.0 | 1.0 |
| 2 | 2.0 | 2.0 | 1.0 | 2.0 |
| 3 | 1.0 | 2.0 | 2.0 | 1.0 |
| 4 | 1.0 | 3.0 | 2.0 | 1.0 |
| 5 | 0.0 | 2.0 | 3.0 | 0.0 |
| 6 | 0.0 | 3.0 | 2.0 | 2.0 |
| Avg. Level | 1.0 | 2.5 | 1.8 | 1.2 |

TABLE 7-2

Figure 5B:
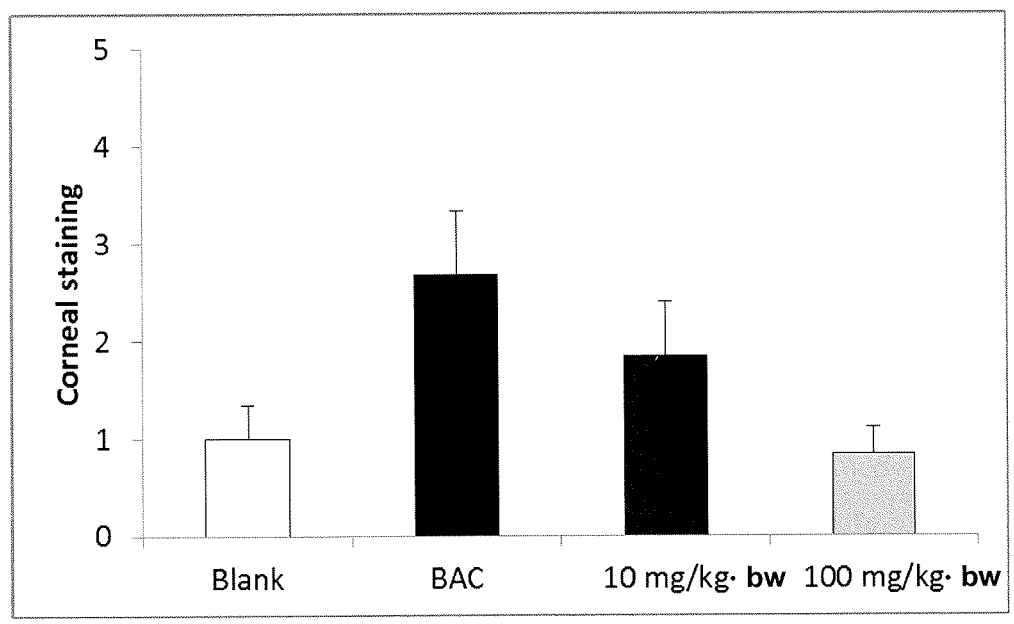

Average level of corneal staining of BAC mice
(Corresponding with FIG. 5B)

| Mouse | Group | | | |
|---|---|---|---|---|
| | Blank | BAC | 10 mg/kg · bw | 100 mg/kg · bw |
| 1 | 1.0 | 2.0 | 3.0 | 1.0 |
| 2 | 0.0 | 2.0 | 2.0 | 1.0 |

TABLE 7-2-continued

Average level of corneal staining of BAC mice
(Corresponding with FIG. 5B)

| Mouse | Group | | | |
|---|---|---|---|---|
| | Blank | BAC | 10 mg/kg · bw | 100 mg/kg · bw |
| 3 | 1.0 | 2.0 | 2.0 | 1.0 |
| 4 | 2.0 | 3.0 | 1.0 | 1.0 |
| 5 | 1.0 | 3.0 | 2.0 | 0.0 |
| 6 | 1.0 | 4.0 | 1.0 | 1.0 |
| Avg. Level | 1.0 | 2.7 | 1.8 | 0.8 |

Figure 6A:
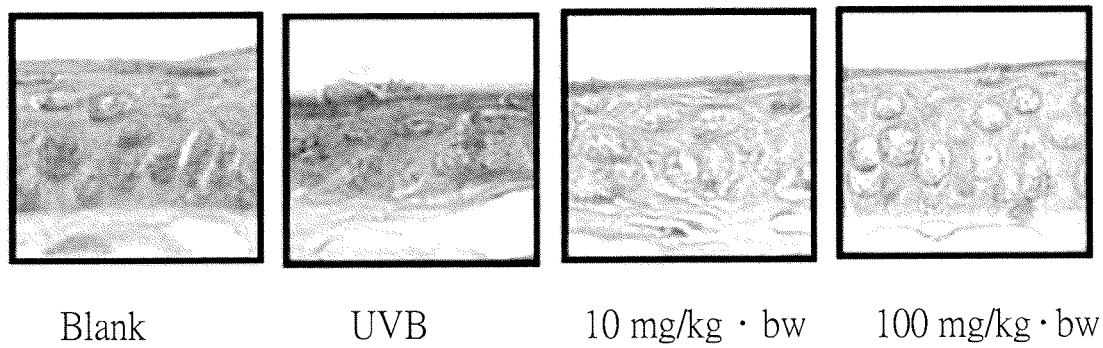
FIG. 6A and FIG. 6B show the test results of H-E stain in mice.
Figure 6B:
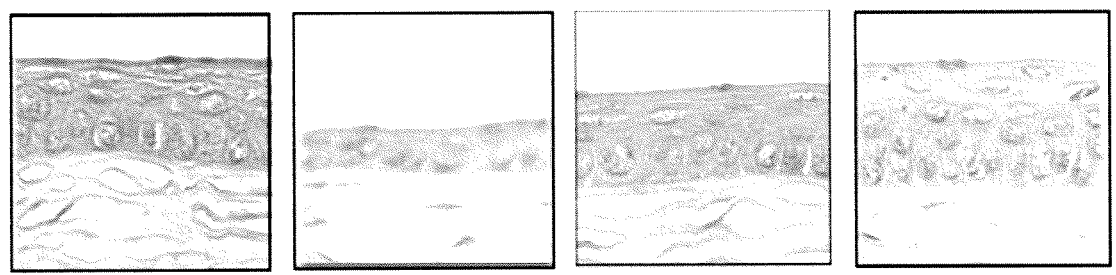

3. The corneal sections were stained with hematoxylin and eosin (HE). The result is shown in FIG. 6A and FIG. 6B. The result shows that in both BAC and UVB tests, the mice of experimental groups (feeding the *C. cicadae* mycelium active substances) have higher and thicker cell layers than those of the blank control group. Thus, it is good for preventing xerophthalmia.

4. The tear film break up time is a test to measure the relative stability of the precorneal tear film. The result is shown in Tables 8-1 to 8-4 (corresponding with FIGS. 7A to 7D). The result shows that in both BAC and UVB tests, the mice of experimental groups (feeding the *C. cicadae* active substances) have higher TBUT and relative TBUT than those of the blank control group. Thus, it is good for preventing xerophthalmia.

TABLE 8-1

Figure 7A:
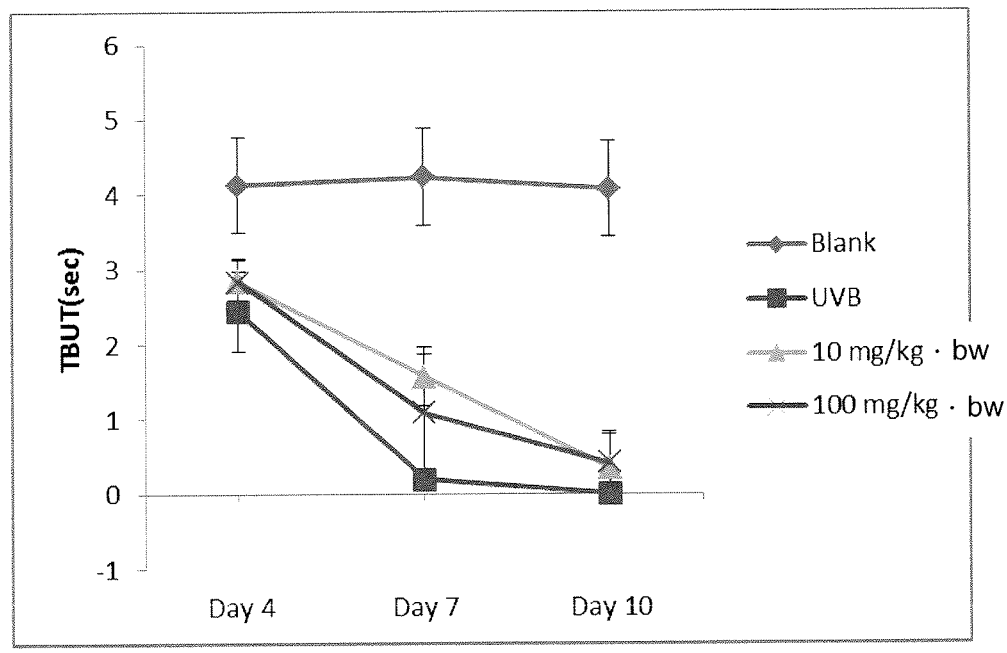
FIG. 7A to FIG. 7D show the test results of tear film breakup time (TBUT) in mice (corresponding with Table 8-1 to Table 8-4).

Tear film breakup time (sec.) of UVB mice
(Corresponding with FIG. 7A)

| Group | Day 4 | Day 7 | Day 10 |
|---|---|---|---|
| Blank | 4.13 | 4.24 | 4.08 |
| UVB | 2.44 | 0.19 | 0.00 |
| 10 mg/kg · bw | 2.83 | 1.56 | 0.35 |
| 100 mg/kg · bw | 2.83 | 1.08 | 0.41 |

TABLE 8-2

Figure 7B:
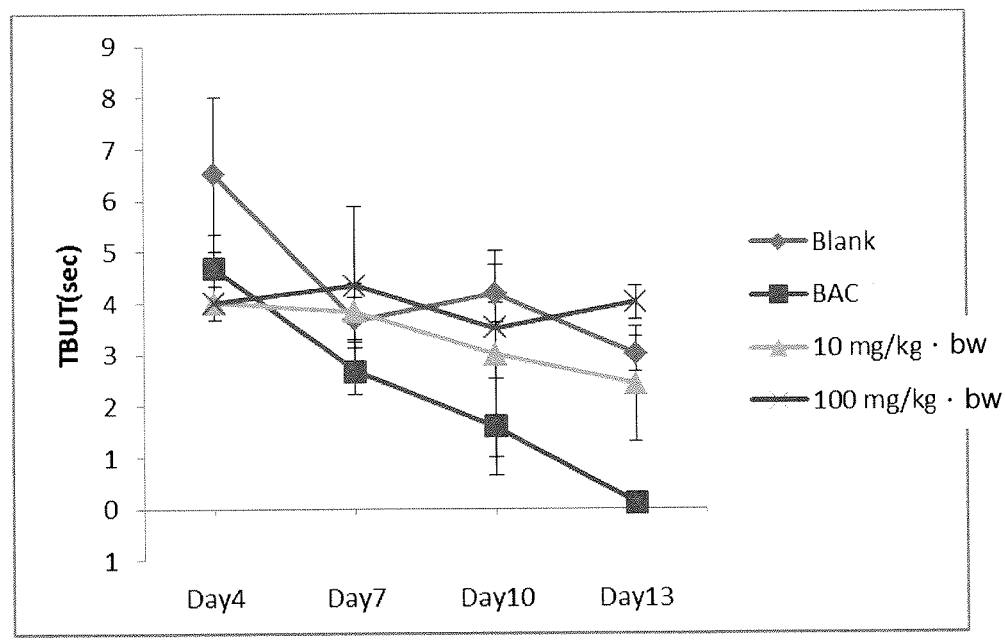

Tear film breakup time (sec.) of BAC mice
(Corresponding with FIG. 7B)

| Group | Day 4 | Day 7 | Day 10 | Day 13 |
|---|---|---|---|---|
| Blank | 6.50 | 3.67 | 4.17 | 3.00 |
| BAC | 4.67 | 2.67 | 1.58 | 0.10 |
| 10 mg/kg · bw | 4.00 | 3.83 | 3.00 | 2.42 |
| 100 mg/kg · bw | 4.00 | 4.33 | 3.50 | 4.0 |

TABLE 8-3

Figure 7C:
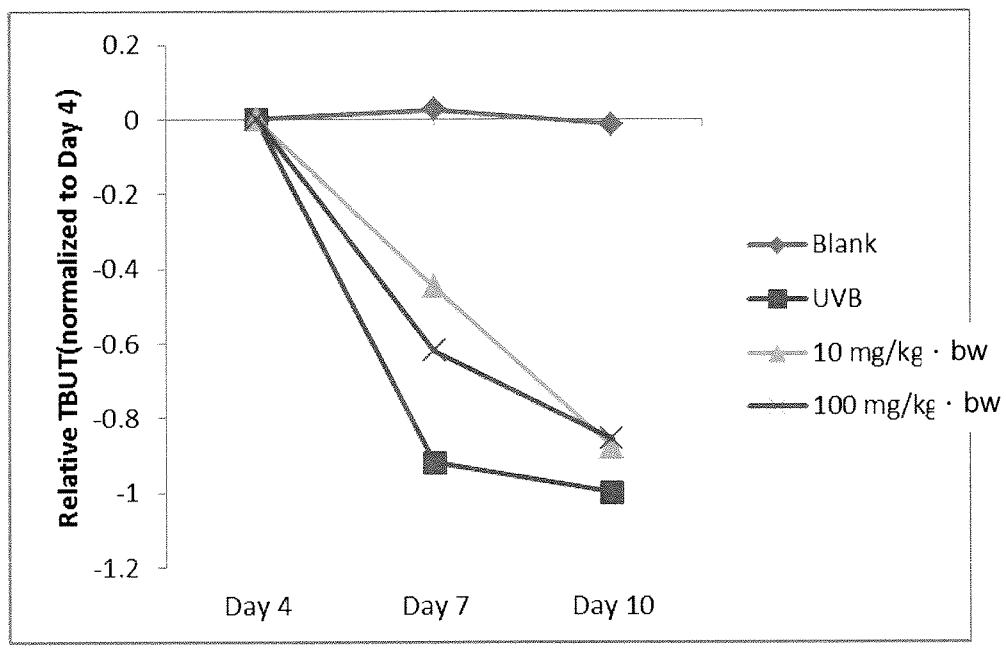

Relative tear film breakup time (sec.) of UVB mice
(Corresponding with FIG. 7C)

| Group | Day 4 | Day 7 | Day 10 |
|---|---|---|---|
| Blank | 0.00 | 0.03 | −0.01 |
| UVB | 0.00 | −0.92 | −1.00 |
| 10 mg/kg · bw | 0.00 | −0.45 | −0.88 |
| 100 mg/kg · bw | 0.00 | −0.62 | −0.86 |

TABLE 8-4

Figure 7D:
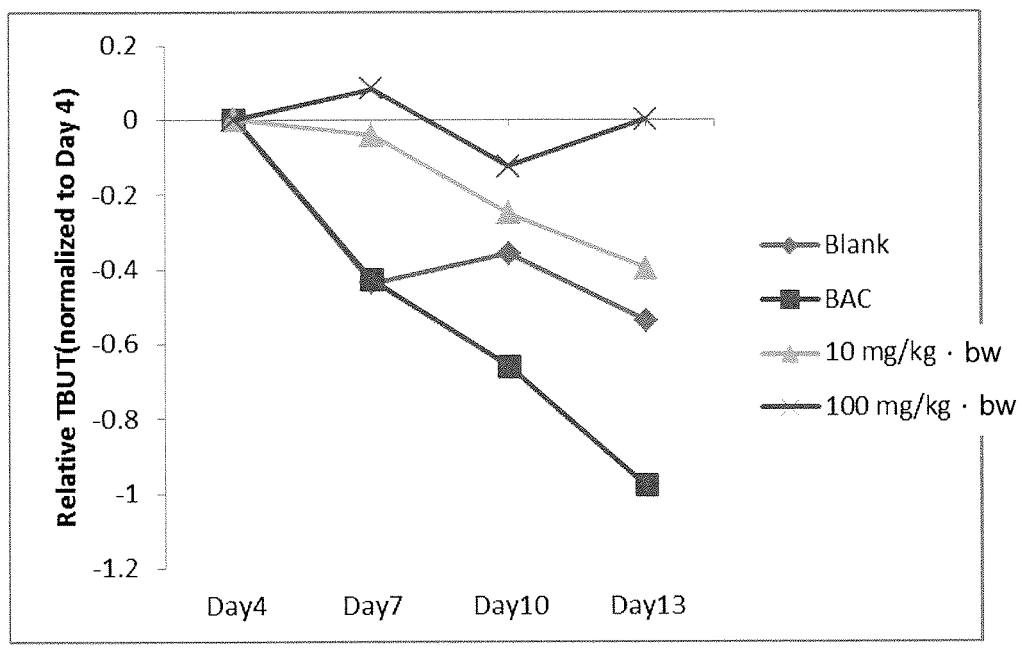

Relative tear film breakup time (sec.) of BAC
mice (Corresponding with FIG. 7D)

| Group | Day 4 | Day 7 | Day 10 | Day 13 |
|---|---|---|---|---|
| Blank | 0.00 | −0.44 | −0.36 | −0.54 |
| BAC | 0.00 | −0.43 | −0.66 | −0.98 |
| 10 mg/kg · bw | 0.00 | −0.04 | −0.25 | −0.40 |
| 100 mg/kg · bw | 0.00 | 0.08 | −0.13 | 0.00 |

5. Corneal sensitivity uses Cochet and Bonnet aesthesiometer to measure the corneal sensitivity. The result is shown in Table 9-1 and 9-2 (corresponding with FIG. 8A and FIG. 8B). The result shows that in both BAC and UVB tests, the mice of experimental groups (feeding *C. cicadae* mycelium active substances) have lower corneal sensitivity than those of the blank control group. Thus, it is good for preventing xerophthalmia.

TABLE 9-1

Figure 8A:
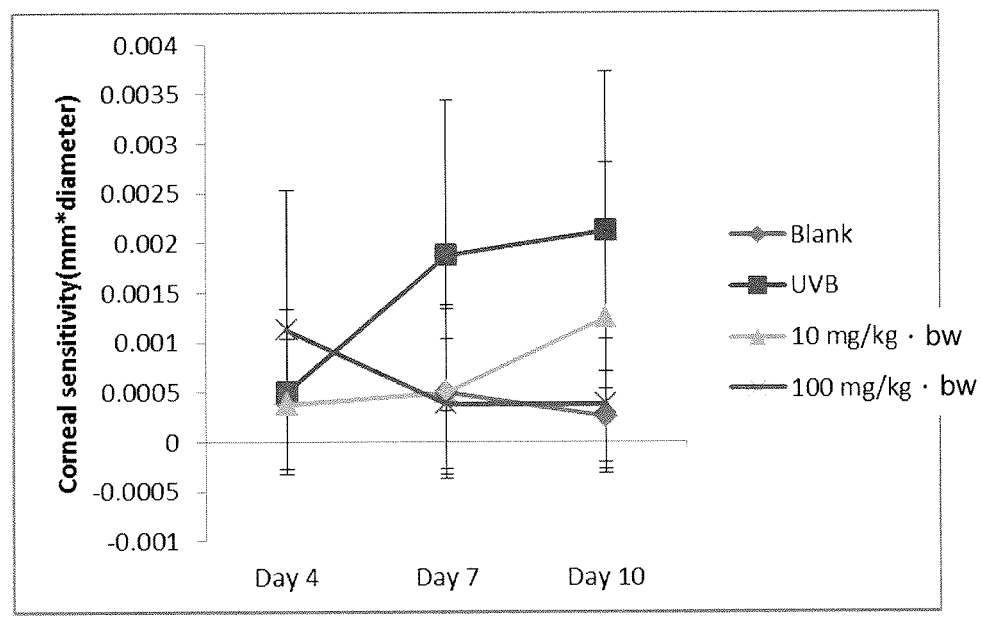
FIG. 8A and FIG. 8B show the test results of corneal sensitivity test in mice (corresponding with Table 9-1 and Table 9-2).

Average level of corneal sensitivity (mm) of UVB
mice (Corresponding with FIG. 8A)

| Group | Day 4 | Day 7 | Day 10 |
|---|---|---|---|
| Blank | 0.000375 | 0.000500 | 0.000250 |
| UVB | 0.000500 | 0.001875 | 0.002125 |
| 10 mg/kg · bw | 0.000375 | 0.000500 | 0.001250 |
| 100 mg/kg · bw | 0.001125 | 0.000375 | 0.000375 |

TABLE 9-2

Figure 8B:
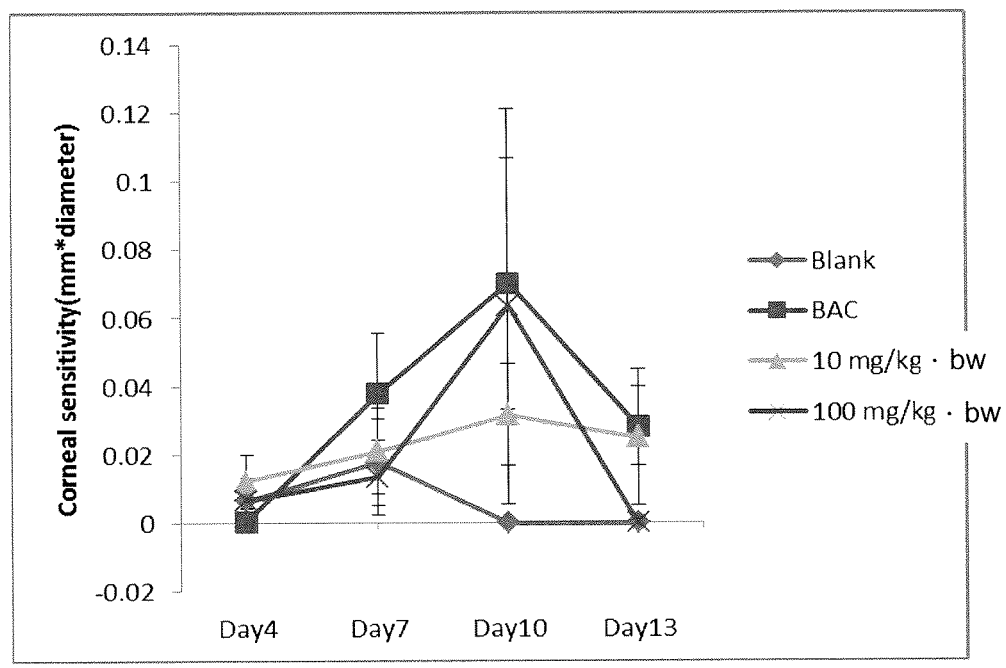

Average level of corneal sensitivity (mm) of BAC
mice (Corresponding with FIG. 8B)

| Group | Day 4 | Day 7 | Day 10 | Day 13 |
|---|---|---|---|---|
| Blank | 0.006667 | 0.017778 | 0.000000 | 0.000000 |
| BAC | 0.000444 | 0.037778 | 0.070000 | 0.028333 |
| 10 mg/kg · bw | 0.012222 | 0.021111 | 0.031667 | 0.025000 |
| 100 mg/kg · bw | 0.006667 | 0.013333 | 0.063333 | 0.000000 |

Example 3 proves that the *C. cicadae* mycelium active substances made from the above example is effective for treating xerophthalmia induced by physical or chemical damages. Thus, the *C. cicadae* mycelium active substances of the present invention could be used for eye care, treatment and prevention for xerophthalmia.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A method of preparing a mixture of *Cordyceps cicadae* mycelium active substances for preventing and/or treating xerophthalmia, wherein the method comprises following steps:
   (a) culturing a *Cordyceps cicadae* mycelium in a plate media at 15 to 35° C. for 5 to 14 days;
   (b) inoculating the *Cordyceps cicadae* mycelium of step (a) to a flask containing liquid media and culturing the mycelium at 15 to 35° C. with a pH of 2 to 8 for 3 days;
   (c) inoculating the *Cordyceps cicadae* mycelium of step (b) to a fermenter tank and culturing the mycelium at 15 to 35° C. with a pH of 2 to 8 for 3 days, so as to obtain a *Cordyceps cicadae* mycelium fermentation liquid;

(d) freeze-drying and grating the *Cordyceps cicadae* mycelium fermentation liquid, so as to obtain a *Cordyceps cicadae* mycelium powder;

(e) dividing the *Cordyceps cicadae* mycelium powder into two parts, extracting one part of the *Cordyceps cicadae* mycelium powder with water and extracting the other part of the *Cordyceps cicadae* mycelium powder with alcohol separately, so as to obtain a *Cordyceps cicadae* mycelium water extract and a *Cordyceps cicadae* mycelium alcohol extract; and (f) drying the *Cordyceps cicadae* mycelium water extract and the *Cordyceps cicadae* mycelium alcohol extract, and mixing the water extracts and the alcohol extracts, so as to obtain the mixture of *Cordyceps cicadae* mycelium active substances.

2. The method of claim 1, wherein the culturing process of step (b) is shake flask cultivation, and the flask is shaking at a speed range between 10 and 250 rpm.

3. The method of claim 1, wherein in step (c), the gas feed in the fermenter tank comprises air, oxygen, carbon dioxide, helium or a combination thereof.

4. The method of claim 1, wherein in step (c), the pressure of the fermenter tank is at 0.5 to 1.0 kg/cm2, and the gas flow rate of fermenter tank is 0.01 to 1.5 VVM.

5. The method of claim 1, wherein the liquid media used in step (b) and step (c) are the same, and the liquid media comprises grains, beans, inorganic salts, carbohydrates, yeast extract, malt extract or a combination thereof.

6. The method of claim 1, wherein the alcohol is methanol or ethanol.

7. The method of claim 1, wherein the mixture of *Cordyceps cicadae* mycelium active substances comprise the same weight of the water extracts and the alcohol extracts from the *Cordyceps cicadae* mycelium powder.

8. A mixture of *Cordyceps cicadae* mycelium active substances for preventing and/or treating xerophthalmia, wherein the mixture is prepared by a method comprising:

(a) culturing a *Cordyceps cicadae* mycelium in a plate media at 15 to 35° C. for 5 to 14 days;

(b) inoculating the *Cordyceps cicadae* mycelium of step (a) to a flask containing liquid media and culturing the mycelium at 15 to 35° C. with a pH of 2 to 8 for 3 days;

(c) inoculating the *Cordyceps cicadae* mycelium of step (b) to a fermenter tank and culturing the mycelium at 15 to 35° C. with a pH of 2 to 8 for 3 days, so as to obtain a *Cordyceps cicadae* mycelium fermentation liquid;

(d) freeze-drying and grating the *Cordyceps cicadae* mycelium fermentation liquid, so as to obtain a *Cordyceps cicadae* mycelium powder;

(e) dividing the *Cordyceps cicadae* mycelium powder into two parts, extracting one part of the *Cordyceps cicadae* mycelium powder with water and extracting the other part of the *Cordyceps cicadae* mycelium powder with alcohol separately, so as to obtain a *Cordyceps cicadae* mycelium water extract and a *Cordyceps cicadae* mycelium alcohol extract and (f) drying the *Cordyceps cicadae* mycelium water extract and the *Cordyceps cicadae* mycelium alcohol extract, and mixing the water extracts and the alcohol extracts, so as to obtain the mixture of *Cordyceps cicadae* mycelium active substances.

9. A pharmaceutical composition for preventing and/or treating xerophthalmia, which comprises a therapeutically effective amount of the mixture of *Cordyceps cicadae* mycelium active substances of claim 8 and a pharmaceutically acceptable carrier, excipient, diluents or adjuvant.

* * * * *